US010080584B2

(12) United States Patent
Miller (10) Patent No.: US 10,080,584 B2
(45) Date of Patent: Sep. 25, 2018

(54) SYSTEM AND METHOD FOR RECEIVING TUBE FORCEPS FOR USE IN BODY PIERCINGS

(71) Applicant: Timothy L. Miller, Scottsdale, AZ (US)

(72) Inventor: Timothy L. Miller, Scottsdale, AZ (US)

( * ) Notice: Subject to any disclaimer, the term of this patent is extended or adjusted under 35 U.S.C. 154(b) by 371 days.

(21) Appl. No.: 14/958,324

(22) Filed: Dec. 3, 2015

(65) Prior Publication Data

US 2017/0156752 A1 Jun. 8, 2017

(51) Int. Cl.
*A61B 17/34* (2006.01)
*A61B 17/28* (2006.01)
*A44C 15/00* (2006.01)

(52) U.S. Cl.
CPC ...... *A61B 17/3403* (2013.01); *A44C 15/0035* (2013.01); *A61B 17/2833* (2013.01); *A61B 17/2841* (2013.01); *A61B 2017/3405* (2013.01)

(58) Field of Classification Search
CPC ........ A61B 17/3403; A61B 2017/3405; A61B 2017/3407; A61B 2017/3409; A61B 2017/3411; A61B 17/3201; A61B 18/1445; A61B 2018/146; A61B 17/285; A61B 17/295
See application file for complete search history.

(56) References Cited

U.S. PATENT DOCUMENTS

| 127,646 | A | 6/1872 | Schlarbaum |
| 652,175 | A | 6/1900 | Felson |
| 1,422,538 | A | 7/1922 | Cameron |
| 3,916,909 | A | 11/1975 | Kletschka et al. |
| 4,608,982 | A | 9/1986 | Pollard |
| 5,071,428 | A | 12/1991 | Fogarty |
| 5,300,087 | A | 4/1994 | Knoepfler |
| 5,569,271 | A | 10/1996 | Hoel |
| 5,919,206 | A * | 7/1999 | Gengler ............... A61B 17/295 606/170 |
| 6,241,740 | B1 * | 6/2001 | Davis ................. A61B 17/1227 606/139 |
| 7,208,004 | B2 | 4/2007 | Murdoch |
| 7,402,166 | B2 * | 7/2008 | Feigl ................. A61B 17/0482 606/144 |
| 8,573,220 | B2 | 11/2013 | Karling et al. |
| 8,757,467 | B2 * | 6/2014 | Racenet ............... A61B 17/072 227/180.1 |

(Continued)

FOREIGN PATENT DOCUMENTS

WO 2009092815 A2 7/2009

OTHER PUBLICATIONS http://www.v-tech.se/wp-content/uploads/2010/07/Sutureaid_8pp_A5_170510.pdf.

*Primary Examiner* — Jonathan Miles
(74) *Attorney, Agent, or Firm* — Evan Schechter (57) ABSTRACT

A system and method for body piercings using body piercing forceps. The body piercing forceps comprises two arms pivotally hinged to each other. One arm comprises a needle guide at the end of the arm that may be placed externally on the body. The other arm comprises a receiving tube that may be placed into a body orifice. The body piercing forceps allow complete control over the location of a body piercing and prevent dangerous complications that may arise from traditional piercings.

18 Claims, 5 Drawing Sheets

(56) References Cited

U.S. PATENT DOCUMENTS

| | | | |
|---|---|---|---|
| 2002/0099368 A1* | 7/2002 | Schulze | A61B 18/1445 606/45 |
| 2002/0183734 A1* | 12/2002 | Bommannan | A61B 18/1445 606/32 |
| 2004/0186348 A1* | 9/2004 | Kidooka | A61B 10/06 600/104 |
| 2004/0225305 A1* | 11/2004 | Ewers | A61B 1/00135 606/153 |
| 2005/0149016 A1* | 7/2005 | Rizvi | A61B 18/1445 606/51 |
| 2005/0250986 A1* | 11/2005 | Rothe | A61B 1/0014 600/102 |
| 2005/0251162 A1* | 11/2005 | Rothe | A61B 1/0014 606/153 |
| 2007/0255277 A1* | 11/2007 | Nobis | A61B 17/320016 606/45 |
| 2008/0009858 A1* | 1/2008 | Rizvi | A61B 10/06 606/48 |
| 2009/0005795 A1 | 1/2009 | Giap | |
| 2009/0112246 A1* | 4/2009 | Weisshaupt | A61B 17/285 606/174 |
| 2010/0030248 A1* | 2/2010 | Palmer | A61B 17/285 606/169 |
| 2011/0082456 A1* | 4/2011 | Welt | A61B 17/295 606/45 |
| 2012/0041457 A1 | 2/2012 | De Vries et al. | |
| 2014/0005653 A1* | 1/2014 | Shelton, IV | A61B 18/1442 606/33 |
| 2015/0073451 A1* | 3/2015 | Guba | A61B 18/1445 606/167 |
| 2015/0080925 A1* | 3/2015 | Schulte | A61B 17/285 606/169 |
| 2015/0265305 A1* | 9/2015 | Stulen | A61B 17/320068 606/169 |
| 2015/0374396 A1* | 12/2015 | Strobl | A61B 18/1445 606/207 |

* cited by examiner

SYSTEM AND METHOD FOR RECEIVING TUBE FORCEPS FOR USE IN BODY PIERCINGS

BACKGROUND OF THE INVENTION

Field of the Invention

The present invention relates to devices used for body piercings, and more particularly to a system and method for body piercings using forceps comprising at least one receiving tube and at least one needle guide.

Description of Related Art

There is a large need for accurate and safe body piercing instruments. According to one set of statistics, 14% of Americans, around 42 million people, have body piercings aside from earlobes. Among those, 2% of women and 3% of men have genital piercings. In addition, 31% of piercings had unnecessary complications.

Currently, anyone, physically male or female (or a combination thereof), opting to have his or her genitals pierced is taking an unnecessary risk. The current state of the art is to insert a separate receiving tube internally (in the urethra or other orifice) and hope to pierce the skin externally in the correct location. If the piercer misses the unseen receiving tube, dangerous and painful medical complications may arise.

So as to reduce the complexity and length of the Detailed Specification, and to fully establish the state of the art in certain areas of technology, Applicant(s) herein expressly incorporate(s) by reference all of the following materials identified in each numbered paragraph below.

Prior art has described a variety of embodiments of a pair of surgical forceps which contain an integrated needle retention means. These apparatuses are inadequate for body piercing, as they do not contain a receiving tube or a guide for receiving the piercing needle. The described apparatuses cannot be used effectively for body piercing.

Prior art has described a surgical forceps for suturing tissue. The described invention is inadequate for body piercing, as it does not contain a receiving tube or needle guide. It cannot be used effectively for body piercing.

Prior art has described a docking device for a suturing needle attached to surgical instruments. This device is inadequate for body piercing, as a body-piercing needle should not be attached to a forceps. This device cannot be used effectively for body piercing.

Prior art has described a device useful for performing a tracheotomy. This device is inadequate for body piercing in that it can only be used within the trachea and requires anesthesia. This device cannot be used effectively for genital body piercing.

Prior art has described a device for holding and manipulating a surgical needle. This device is inadequate for body piercing as it is not inserted into a body orifice and cannot be used effectively for body piercing.

BRIEF SUMMARY OF THE INVENTION

The present invention provides among other things a system and method for body piercing using a body piercing forceps. It is an objective of the invention to safely provide a system and method for body piercing that is safer, more economical, and easier on the body being pierced than existing body piercing methods. It is a further objective of the invention to provide a system for performing body piercings using one hand for performing tasks that have previously required two or more hands. The system and method can be used anywhere on the body but may work especially well on genital piercings.

The above and other objectives may be achieved using systems involving a first arm and a second arm wherein each arm comprises a hand-gripping end, a distal end, a longitudinal axis, and a joint fixed between the hand-gripping end and the distal end. The first and second arms are pivotally hinged to each other at a joint along their lengths between their hand-gripping ends and their distal ends. The distal end of the first arm further comprises a needle guide, wherein the needle guide comprises an aperture. The distal end of the second arm further comprises a hollow substantially cylindrical receiving tube along a longitudinal axis between the joint and the distal end, wherein the receiving tube is adapted to insert into a body orifice. When the first arm distal end and second arm distal end are in proximity, the needle guide and receiving tube align to allow a needle tip to pass through the needle guide and into the receiving tube.

Some aspects of the invention may include the first arm and second arm being comprised of metal and/or plastic material.

Some aspects of the invention may include a locking mechanism to fix the relative positions of the first arm and second arm.

Some aspects of the invention may include a locking mechanism, which comprises a first fastener on the first arm hand-gripping end and a second fastener on the second arm hand-gripping end, whereby the first and second fasteners secure together.

Some aspects of the invention may include the needle guide comprising a square axial cross-section, a substantially rectangular axial cross-section, a substantially triangular axial cross-section, or a substantially circular axial cross section.

Some aspects of the invention may include the receiving tube comprising one or both of an outside and inside diameter. The outside diameter being between 18 gauge and 0 gauge. 18 gauge is equivalent to approximately 1.0237 mm. 0 gauge is equivalent to approximately 8.2515 mm. The diameter of a gauge in millimeters is equal to 0.127 times 92 to the power of 36 minus the gauge number, divided by 39. In equation form, $D\ (mm) = 0.127\ mm \times 92^{((36-gauge)/39)}$. The inside diameter being between 16 gauge and 2 gauge, equivalent to 1.29 mm and 6.544 mm, respectively.

Some aspects of the invention may include the first arm distal end comprising a concave curvature, or being substantially straight.

The above and other objectives may be achieved by using a method of using a body piercing forceps comprising inserting a receiving tube into a body orifice, whereby the receiving tube includes a hollow tube with an open end; placing a needle guide over a piercing location; wherein the needle guide and receiving tube are coupled via a hinged joint into a forceps adapted for manual control; closing the forceps to align the receiving tube open end with the needle guide whereby a portion of tissue is captured between the receiving tube and the needle guide; passing a needle tip through an aperture in the needle guide; piercing the portion of tissue captured between the needle guide and receiving tube; and advancing the needle tip into the open end of the receiving tube.

The above and other objectives may be achieved by using methods wherein the step of closing the forceps further comprises the step of locking the relative positions of the needle guide and the receiving tube using a locking mechanism.

The above and other objectives may be achieved by using methods wherein the receiving tube includes a first handle opposite the open end and the needle guide includes a second handle opposite the aperture; whereby the step of closing the forceps comprises moving the first handle and the second handle towards one another.

The above and other objectives may be achieved by using methods wherein the step of closing comprises squeezing the first handle and the second handle with fingers of a single hand.

The above and other objectives may be achieved by using methods wherein the step of closing the forceps includes the step of pinching the portion of tissue between the needle guide and the receiving tube.

The above and other objectives may be achieved by using methods wherein the portion of tissue is comprised of tissue in the genital area.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventor is fully aware that he can be his own lexicographer if desired. The inventor expressly elects, as his own lexicographer, to use only the plain and ordinary meaning of terms in the specification and claims unless he clearly states otherwise and then further, expressly sets forth the "special" definition of that term and explain how it differs from the plain and ordinary meaning. Absent such clear statements of intent to apply a "special" definition, it is the inventor's intent and desire that the simple, plain and ordinary meaning to the terms be applied to the interpretation of the specification and claims.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. It should be noted that there are many different and alternative configurations, devices and technologies to which the disclosed inventions may be applied. The full scope of the inventions is not limited to the examples that are described below.

Figure 1:
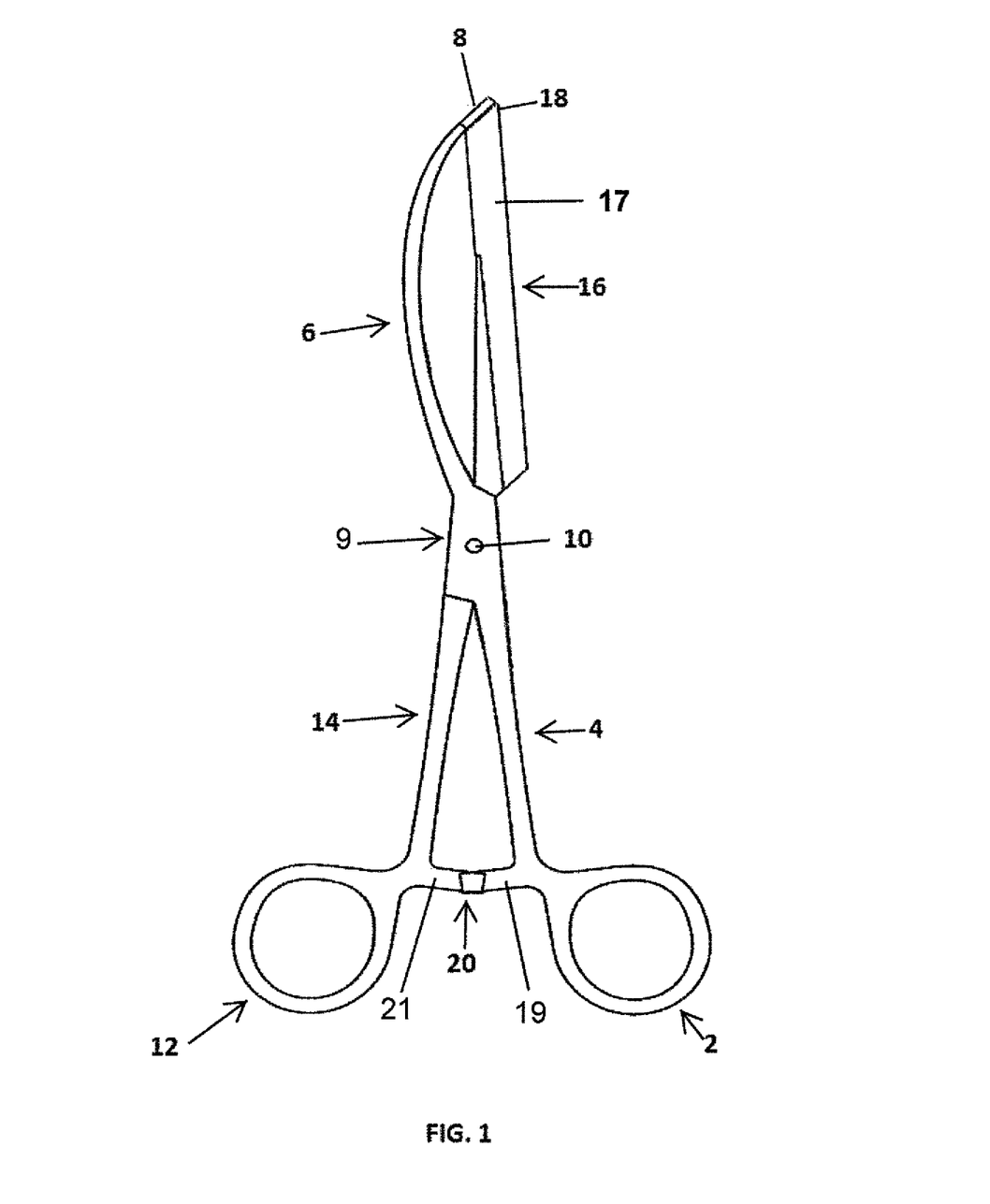
FIG. 1 depicts a side view of a possible embodiment of the present invention in a closed position.

An embodiment of the invention is shown in FIG. 1. A body piercing forceps may comprise the following: A first arm comprising a hand gripping end 2, a distal end 6, a longitudinal axis along 4 between the hand-gripping end 2 and the distal end 6, and a joint 9 fixed between the hand-gripping end 2 and the distal end 6, the joint 9 further comprising a joint bearing 10, the first arm joint at 9 adapted for pivotally hinging with a second arm. The first arm distal end 6 further comprising a needle guide 8 wherein the needle guide comprises an aperture whereby a piercing needle can pass through the needle guide 8. A second arm comprising a hand gripping end 12, a distal end 16, a longitudinal axis along 14 between the hand-gripping end 12 and the distal end 16, and a second arm joint at 9 adapted for pivotally hinging with the first arm joint at 9. The second arm distal end further comprises a hollow substantially cylindrical receiving tube 17 along a longitudinal axis between the second arm joint at 9 and the second arm distal end 16 adapted to insert into a body orifice. The receiving tube must have an opening 18 at the second arm distal end so that when the first arm distal end 6 and the second arm distal end 16 are in proximity, the needle guide 8 and receiving tube opening 18 align to allow a needle tip or point to pass through the needle guide 8 into the receiving tube 17 through the opening 18. Various body piercings may be safely and easily performed in this manner.

The first arm distal end 6 may have a concave curvature or be substantially straight. The needle guide 8 may have a substantially circular axial cross-section. The needle guide 8 may be at an angle relative to the longitudinal axis along 4. The aperture in the needle guide 8 should not be substantially larger than the receiving tube opening 18. If the aperture is substantially larger than the opening 18, a needle passing through the aperture may not pass into the receiving tube 17, causing an unnecessary injury. The aperture in the needle guide 8 may be smaller than the receiving tube opening 18.

The receiving tube 17 may have an outside diameter of between 18 gauge and 0 gauge, equivalent to 1.0237 millimeters (mm) and 8.2515 mm, respectively. The receiving tube 17 may have an inside diameter of between 16 gauge and 2 gauge, equivalent to 1.29 mm and 6.544 mm, respectively. The receiving tube 17 and receiving tube opening 18 may have a substantially circular axial cross-section. The receiving tube opening 18 may be at an angle relative to the axial cross-section of the receiving tube 17.

The body piercing forceps may further comprise a locking mechanism 20 that can fix the relative positions of the first arm and the second arm. This locking mechanism 20 may be positioned near the first arm hand gripping end 2 and the second arm hand gripping end 12. The locking mechanism 20 may be comprised of a first fastener 19 on the first arm hand gripping end 2 and a second fastener 21 on the second arm hand gripping end 12 such that the first fastener 19 and the second fastener 21 secure together when they are in proximity. A locking mechanism 20 may be useful in freeing one hand of a person piercing (a piercer) so that the piercer can safely and effectively pierce a body. The locking mechanism 20 may be magnetic, mechanical, electric, or any other mechanism for locking two arms of a forceps together. A first fastener 19 and a second fastener 21 may not be necessary for a locking mechanism 20. For example, a first fastener 19 may be able to lock into an opening on the second arm longitudinal axis along 14. The first fastener 19 and second fastener 21 may also be used to guide the proximal position of the needle guide 8 and receiving tube opening 18 without locking. If the first fastener 19 and the second fastener 21 are fastened together, the needle guide 18 and the receiving tube opening 18 cannot be forced into closer proximity. Any locking mechanism 20 may be able to be released easily so that the first arm distal end 6 and the second arm distal end 16 can be removed from each other's proximity with ease.

The body piercing forceps may be made of any medically safe material, including, but not limited to plastic or metal. The body piercing forceps may be manufactured for one-time use or repeated use, if it is properly sterilized between each use.

Figures 2, 3:
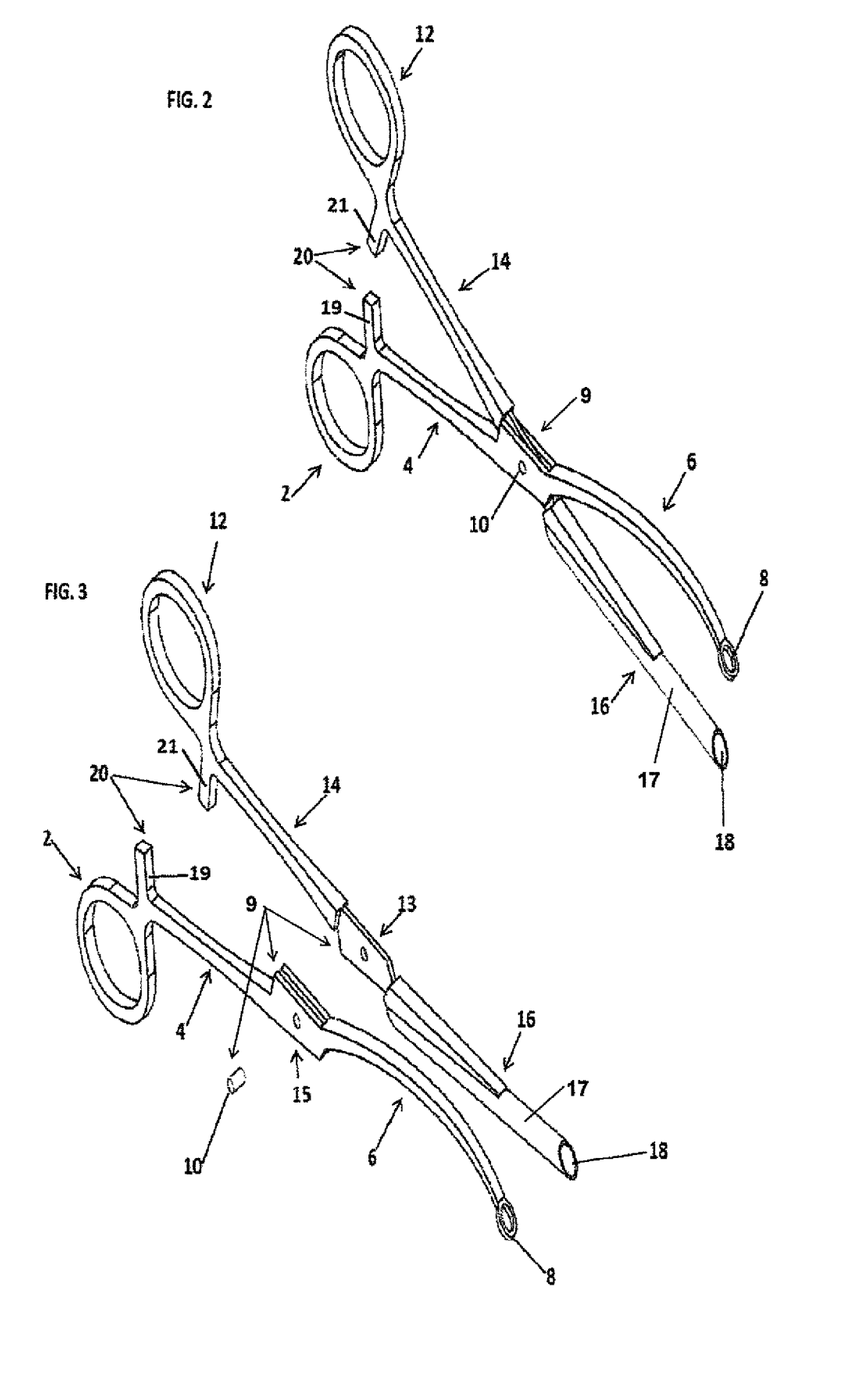
FIG. 2 depicts an isometric view of a possible embodiment of the present invention in an open position.
FIG. 3 depicts an isometric exploded view of a possible embodiment of the present invention.

Referring now to FIG. 2, an isometric view of a possible embodiment of the present invention is shown with needle guide 8 not in proximity with the second arm distal end 16 and opening 18. This view also shows the locking mechanism 20 in an open, unlocked position. The locking mechanism 20 can usually be engaged only when the needle guide 8 and receiving tube opening 18 are in proximity.

Referring now to FIG. 3, an isometric, exploded view of a possible embodiment of the present invention is shown. This view shows a possible embodiment of the joint 9. The joint 9 may consist of a substantially cylindrical joint bearing 10 that allows rotation around the circumference of the cylinder. The first arm and the second arm may be joined together at the joint 9 by a two part joint section 15, with a hole through both parts for joint bearing 10, between the first arm hand-gripping end 2 and the first arm distal end 6. The second arm may have a single part joint section 13, with a hole through it for joint bearing 10, between the second arm hand gripping end 12 and the second arm distal end 16, which fits between the two part joint section 15 on the first arm. By fitting the joint section 13 between the two parts of joint section 15 and inserting joint bearing 10 through both joint sections 13 and 15, a joint 9 allowing pivotally hinged movement of both the first arm and second arm in unison may be formed. Thus, the first arm joint section 15 and the second arm joint section 13 are adapted to pivotally hinge with each other.

Other joints may also be used to effectuate the movement of the first arm and second arm in unison. The joint may also be located at the first arm hand gripping end and the second arm hand gripping end, forming a substantially tweezers-like body piercing forceps wherein the first hand gripping end and the second hand gripping end are the only points where the first arm and second arm meet until the distal end of each arm.

Figure 4:
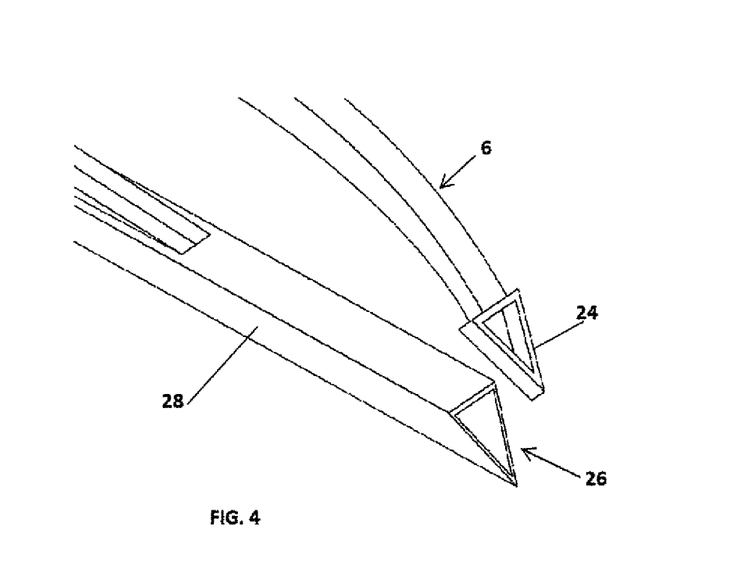
FIG. 4 depicts an isometric view of a portion of a possible embodiment of the present invention with a triangular needle guide.

Referring now to FIG. 4, an isometric view of an alternative embodiment of a portion of the invention is shown. The needle guide 24 at the first arm distal end 6 may be triangular in shape and have a substantially triangular axial cross-section. This shape may help guide a body piercing needle at a particular angle for piercing. The receiving tube 28 may also have a substantially triangular axial cross-section and a substantially triangular opening 26, although a triangular needle guide 24 may be used with a substantially cylindrical receiving tube. The aperture in the needle guide 24 may be smaller than the receiving tube opening 26.

Figure 5:
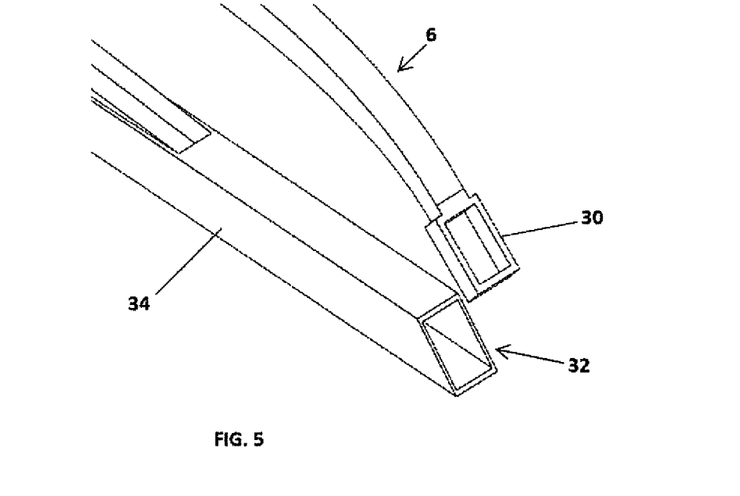
FIG. 5 depicts an isometric view of a portion of a possible embodiment of the present invention with a rectangular needle guide.

Referring now to FIG. 5, an isometric view of an alternative embodiment of a portion of the invention is shown. The needle guide 30 at the first arm distal end 6 may be rectangular in shape and have a substantially rectangular or square axial cross-section. This shape may help guide a body piercing needle at a particular angle for piercing. The receiving tube 34 may also have a substantially rectangular axial cross-section and a substantially rectangular opening 32, although a rectangular needle guide 30 may be used with a substantially cylindrical receiving tube. The aperture in the needle guide 30 may be smaller than the receiving tube opening 32.

Figure 6:
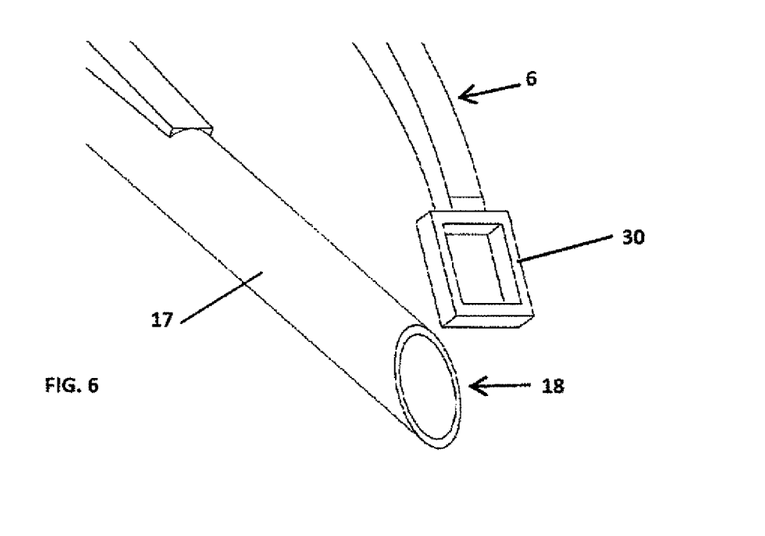
FIG. 6 depicts an isometric view of a portion of a possible embodiment of the present invention with a rectangular needle guide.

Referring now to FIG. 6, an isometric view of an alternative embodiment of a portion of the invention is shown. The needle guide 30 at the first arm distal end 6 may be rectangular in shape and have a substantially rectangular or square axial cross-section. This shape may help guide a body piercing needle at a particular angle for piercing. The receiving tube 17 may have a substantially cylindrical axial cross-section and a substantially circular opening 18. The aperture in the needle guide 30 should not be substantially larger than the opening 18. If the aperture is substantially larger than the opening 18, a needle passing through the aperture may not pass into the receiving tube 17, causing an unnecessary injury. The aperture in the needle guide 30 may be smaller than the receiving tube opening 18.

Figure 7:
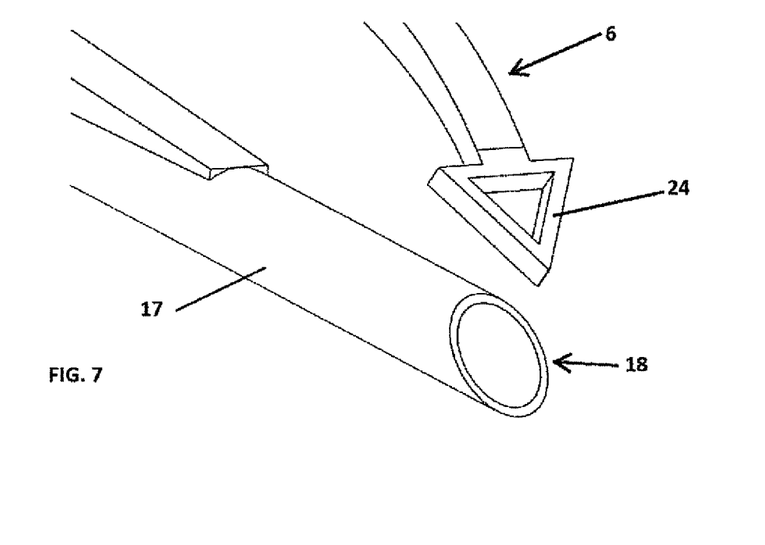
FIG. 7 depicts an isometric view of a portion of a possible embodiment of the present invention with a triangular needle guide.

Referring now to FIG. 7, an isometric view of an alternative embodiment of a portion of the invention is shown. The needle guide 24 at the first arm distal end 6 may be triangular in shape and have a substantially triangular axial cross-section. This shape may help guide a body piercing needle at a particular angle for piercing. The receiving tube 17 may have a substantially cylindrical axial cross-section and a substantially circular opening 18. The aperture in the needle guide 24 should not be substantially larger than the opening 18. If the aperture is substantially larger than the opening 18, a needle passing through the aperture may not pass into the receiving tube 17, causing an unnecessary injury. The aperture in the needle guide 24 may be smaller than the receiving tube opening 18.

Figure 8:
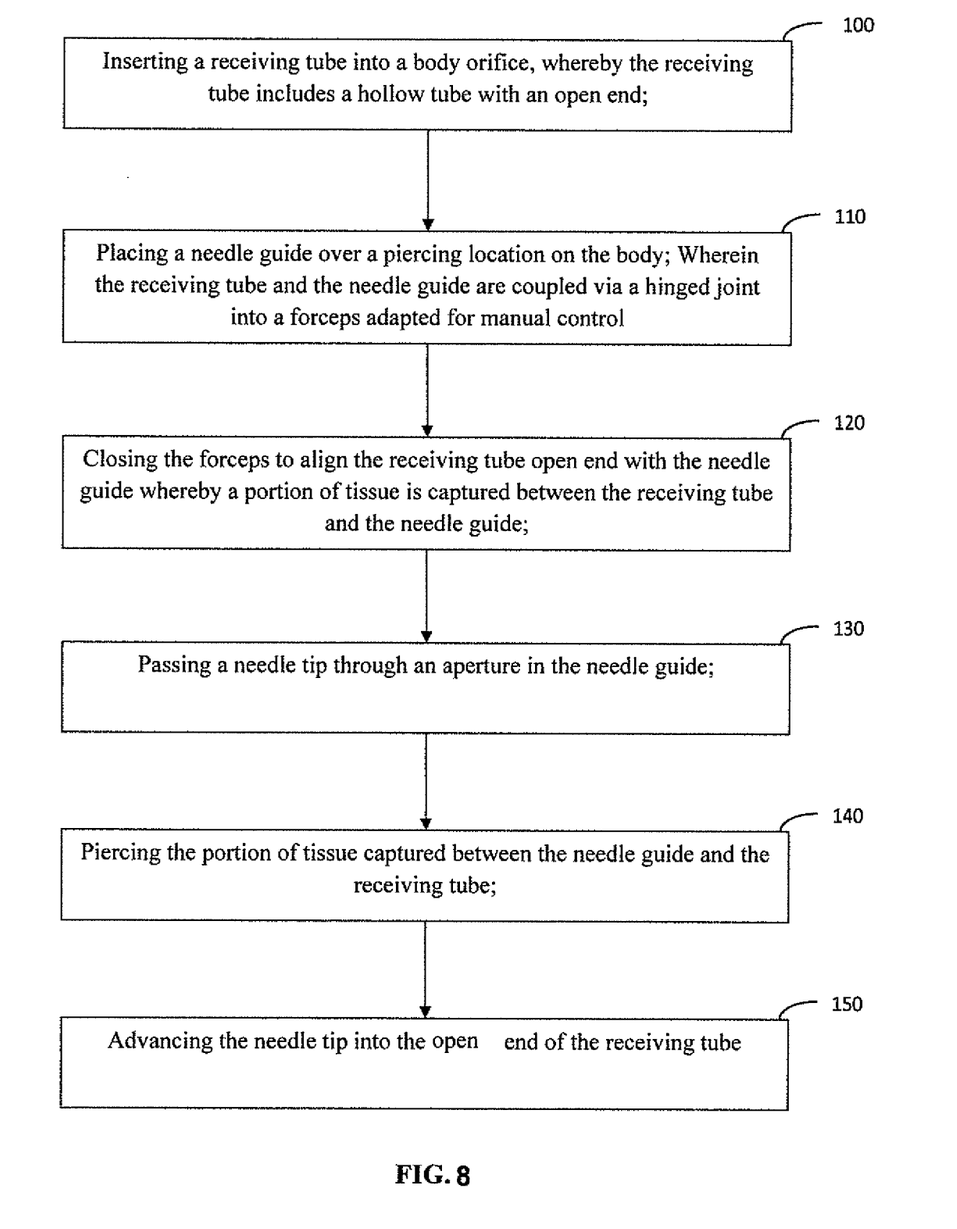
FIG. 8 depicts an example flowchart detailing a method of using the present invention.

Referring now to FIG. 8, an exemplary flowchart detailing a possible method of using the present invention to perform body piercings is shown. An embodiment of the method may be inserting a receiving tube into a body orifice, wherein the receiving tube includes a hollow tube with an open end 100. Next, placing a needle guide over a piercing location on the body, wherein the receiving tube and needle guide are coupled via a hinged joint into a forceps adapted for manual control 110. Next, closing the forceps to align the receiving tube open end with the needle guide and capturing a portion of tissue between the needle guide and receiving tube 120. Next, passing a needle tip through an aperture in the needle guide 130, piercing the portion of tissue captured between the needle guide and receiving tube 140, and advancing the needle tip into the hollow end of the receiving tube 150. After the portion of tissue is pierced by the needle tip, the needle may be removed and the receiving tube removed from the body orifice.

An alternative embodiment may be locking the relative positions of the needle guide and receiving tube through a locking mechanism. The forceps may further comprise a first handle opposite the receiving tube and a second handle opposite the needle guide, whereby moving the first handle and second handle towards one another will force the needle guide and receiving tube to move towards one another, closing the forceps.

In an embodiment, it is possible to close the forceps by squeezing the first handle and second handle using only the fingers of a single human hand. In an embodiment, the portion of tissue between the receiving tube and needle guide is pinched. This step may make it easier and safer to pierce the portion of tissue. The portion of tissue may be in the genital region.

The invention claimed is:

1. A body piercing forceps comprising:
 a first arm and a second arm, the first arm comprising a hand-gripping end, a distal end, a longitudinal axis, and a joint fixed between the hand-gripping end and the distal end, the first arm joint adapted for pivotally hinging with the second arm;
 the first arm distal end further comprising a needle guide wherein the needle guide comprises a closed aperture;
 the second arm comprising a hand-gripping end, a distal end, a longitudinal axis, and a joint fixed between the hand-gripping end and the distal end, the second arm joint adapted for pivotally hinging with the first arm joint;
 the second arm distal end further comprising a hollow substantially cylindrical receiving tube along the second arm longitudinal axis between the second arm joint and the second arm distal end, the receiving tube adapted to insert into a body orifice; and
 wherein when the first arm distal end and the second arm distal end are in proximity, the needle guide and the receiving tube align axially along the second arm longitudinal axis such that the needle guide is distal the receiving tube to allow a needle tip to pass through the needle guide and into the receiving tube.

2. The body piercing forceps of claim 1, further comprising a locking mechanism to fix the relative position of the first arm and the second arm.

3. The body piercing forceps of claim 2, wherein the locking mechanism comprises a first fastener on the first arm hand-gripping end; and further comprises a second fastener on the second arm hand-gripping end; whereby the first fastener and the second fastener secure together.

4. The body piercing forceps of claim 1, wherein the needle guide comprises a square axial cross-section.

5. The body piercing forceps of claim 1, wherein the needle guide comprises a substantially rectangular axial cross-section.

6. The body piercing forceps of claim 1, wherein the needle guide comprises a substantially triangular axial cross-section.

7. The body piercing forceps of claim 1, wherein the needle guide comprises a substantially circular axial cross-section.

8. The body piercing forceps of claim 1, wherein the receiving tube comprises an outside diameter, said outside diameter between 18 gauge and 0 gauge.

9. The body piercing forceps of claim 1, wherein the receiving tube comprises an inside diameter, said inside diameter between 16 gauge and 2 gauge.

10. The body piercing forceps of claim 1, wherein the first arm distal end comprises a concave curvature.

11. The body piercing forceps of claim 1, wherein the first arm distal end is substantially straight.

12. A method for using the body piercing forceps of claim 1, comprising:
 inserting the receiving tube into a body orifice, whereby the receiving tube includes a hollow tube with an open end;
 placing the needle guide over a piercing location;
 wherein the receiving tube and the needle guide are coupled via a hinged joint into a forceps adapted for manual control;
 closing the forceps to align the receiving tube open end with the needle guide whereby a portion of tissue is captured between the receiving tube and the needle guide;
 passing a needle tip through the aperture in the needle guide;
 piercing the portion of tissue captured between the needle guide and the receiving tube; and
 advancing the needle tip into the open end of the receiving tube.

13. The method of claim 12, wherein the step of closing the forceps further comprises the step of locking relative positions of the needle guide and the receiving tube.

14. The method of claim 12 wherein the receiving tube includes a first handle opposite the open end and the needle guide includes a second handle opposite the aperture; whereby the step of closing the forceps comprises moving the first handle and the second handle towards one another.

15. The method of claim 14 wherein the step of closing comprises squeezing the first handle and the second handle with fingers of a single hand.

16. The method of claim 12 wherein the step of closing the forceps includes the step of pinching the portion of tissue between the needle guide and the receiving tube.

17. The method of claim 12 wherein the portion of tissue includes penile tissue.

18. The method of claim 12 wherein the portion of tissue includes vaginal tissue.

* * * * *